United States Patent [19]

Zdrahala

[11] Patent Number: 5,248,305
[45] Date of Patent: Sep. 28, 1993

[54] EXTRUDED TUBING AND CATHETERS HAVING HELICAL LIQUID CRYSTAL FIBRILS

[75] Inventor: Richard J. Zdrahala, Miami Lakes, Fla.

[73] Assignee: Cordis Corporation, Miami Lakes, Fla.

[21] Appl. No.: 933,667

[22] Filed: Aug. 24, 1992

Related U.S. Application Data

[60] Division of Ser. No. 727,890, Jul. 10, 1991, Pat. No. 5,156,785, which is a continuation of Ser. No. 389,794, Aug. 4, 1989, abandoned.

[51] Int. Cl.$^5$ ............................................. A61M 25/00
[52] U.S. Cl. .................................. 604/280; 604/283; 138/153
[58] Field of Search .................. 604/264, 280, 282; 128/656, 658; 138/125, 132, 137, 140, 153; 428/1, 36.9, 36.91

[56] References Cited

U.S. PATENT DOCUMENTS

| | | |
|---|---|---|
| 2,437,542 | 3/1948 | Krippendorf . |
| 3,485,234 | 12/1969 | Stevens . |
| 3,585,707 | 6/1971 | Stevens . |
| 3,772,405 | 11/1973 | Hamb . |
| 3,778,410 | 12/1973 | Kuhfuss et al. . |
| 4,332,759 | 6/1982 | Ide . |
| 4,447,599 | 5/1984 | Cogswell et al. . |
| 4,516,972 | 5/1985 | Samson . |
| 4,577,543 | 3/1986 | Wilson . |
| 4,581,399 | 4/1986 | Yoon . |
| 4,636,346 | 1/1987 | Gold et al. . |
| 4,685,090 | 8/1987 | Krevor . |
| 4,728,698 | 3/1988 | Isayev et al. . |
| 4,729,662 | 3/1988 | O'Brien . |
| 4,734,240 | 3/1988 | Chung et al. . |
| 4,737,153 | 4/1988 | Shimamura et al. . |
| 4,764,324 | 8/1988 | Burnham . |
| 4,790,831 | 12/1988 | Skribiski . |
| 4,817,613 | 4/1989 | Jaraczewski et al. . |
| 4,842,590 | 6/1989 | Tanabe et al. . |
| 4,867,174 | 10/1989 | Skribiski . |
| 4,879,081 | 11/1989 | Keep . |
| 4,898,591 | 2/1990 | Jang et al. . |
| 4,973,442 | 11/1990 | Harvey et al. . |
| 5,059,269 | 10/1991 | Hu et al. . |

FOREIGN PATENT DOCUMENTS

| | | |
|---|---|---|
| 1078308 | 5/1980 | Canada . |
| 2946385 | 5/1981 | Fed. Rep. of Germany ...... 604/282 |
| 8202813 | 2/1984 | Netherlands . |

OTHER PUBLICATIONS

James L. White & John F. Fellers entitled: Macromolecular Liquid Crystals and Their Applications to High--Modulus and Tensile-Strength Fibers, (1978), pp. 137–173.

G. W. Farell and J. F. Fellers entitled A Rotating Annular Die to Control the Biaxial Orientation in Melt Processed Thermotropic Liquid Crystalline Cellulose Derivatives–Journal of Polymer Engineering, vol. 6, Nos. 1–4, 1986, pp. 263–289.

D. G. Baird and R. Ramanathan entitled The in–situ Generation of Liquid Crystalline Reinforcements in Engineering Thermoplastics 22 pages.

Translation of Japanese Patent Appln. No. 63-199622 published on Aug. 18, 1988 Title: Moulding Method for Multilayer Film Patent No. 62-31082, Application Date Feb. 13, 1987.

2 page article LCP Activity Increases: New Suppliers, Products Modern Plastics, Apr., 1989 pp. 166 & 168.

M. Meier entitled The Extrusion of Liquid Crystal Polymers ANTEC, 1989 pp. 200–202.

Primary Examiner—John D. Yasko
Assistant Examiner—Anthony Gutowski
Attorney, Agent, or Firm—Gerstman & Ellis, Ltd.

[57] ABSTRACT

Extruded catheters and other flexible plastic tubing may be manufactured with improved rotational and/or longitudinal stiffness, compared with catheters made of more conventional plastics. A tubing of liquid crystal polymer plastic-containing material may be extruded through a tube extrusion die while rotating the inner and outer die walls to provide circumferential shear to the extruded tube. Thus the liquid crystal polymer is oriented in a helical manner to provide improved properties, including greater rotational stiffness.

19 Claims, 1 Drawing Sheet

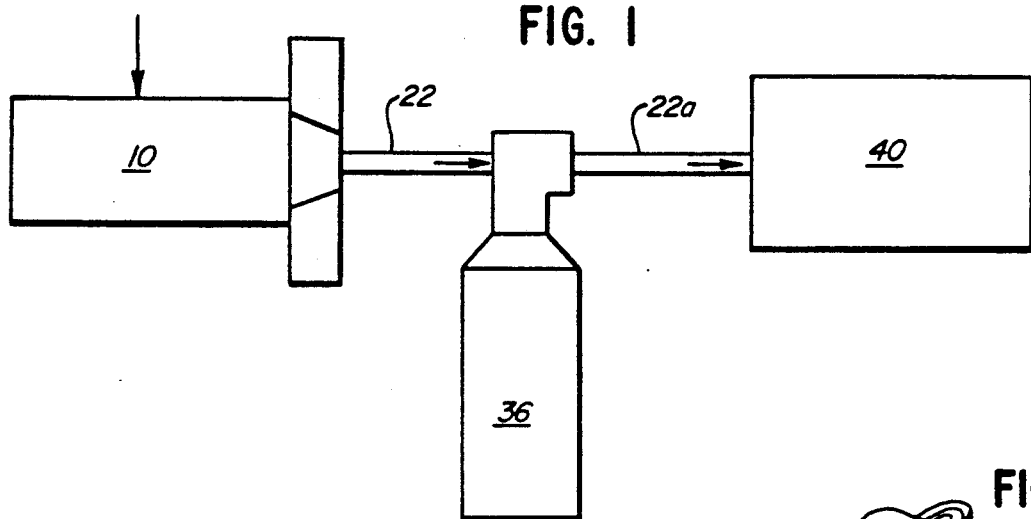
FIG. 1
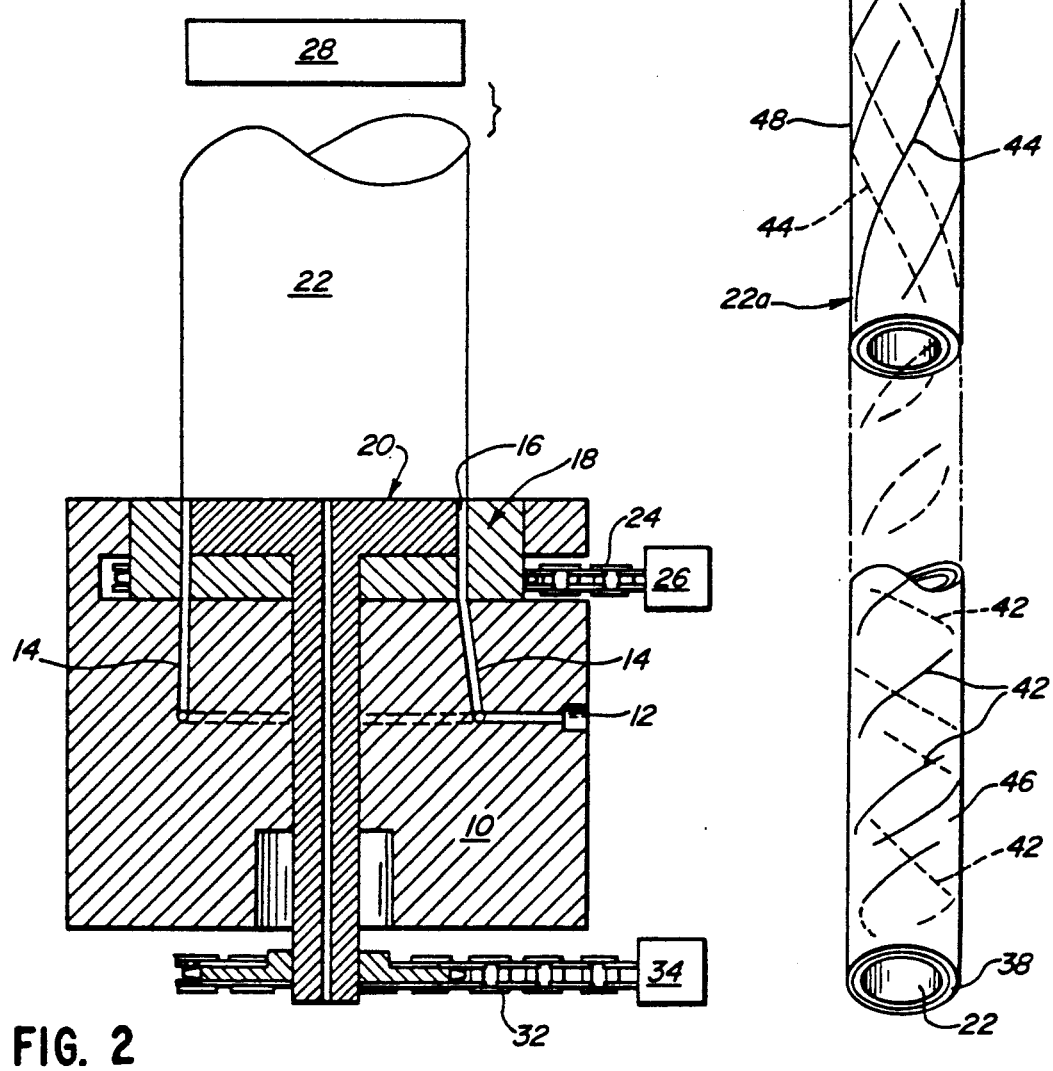
FIG. 2
FIG. 3

EXTRUDED TUBING AND CATHETERS HAVING HELICAL LIQUID CRYSTAL FIBRILS

This is a division of U.S. application Ser. No. 727,890, filed Jul. 10, 1991, (now U.S. Pat. No. 5,156,785), which is a continuation of U.S. application Ser. No. 389,794, filed Aug. 4, 1090 now abandoned.

BACKGROUND OF THE INVENTION

Extruded catheters and other flexible plastic tubing may, in many circumstances, require a greater degree of torsional or rotational stiffness than is normally provided by a conventional plastic material from which a catheter or tube may be extruded, such as polyethylene, polyvinyl chloride, polyurethane, or polyethylene terephthalate. For example, intravascular catheters for heart catheterization or PTCA need to be guided through the branching network of the patient's arterial system. Typically, such catheters may be "steered", in which the physician rotates the catheter, which may have a bent tip, to select a path when a blood vessel junction is encountered. For such a catheter, it is highly desirable to exhibit good rotational stiffness in addition to axial stiffness.

To provide such rotational stiffness, plastic catheters have been manufactured in the prior art with a tubular, braided wire sheath with is typically sealed within the catheter to provide added strength and rotational stiffness, as shown in Stevens U.S. Pat. No. 3,485,234, and 3,585,707, for example. Additionally, as shown in the pending application of Jeffery G. Gold et al., U.S. application Ser. No. 270,810, filed Nov. 14, 1988 and entitled Catheter Having Sections Of Variable Torsion Characteristics, a tubular wire sheath is provided in which the angular relation of the wire strands vary along the length of the catheter, so that different sections of the catheter exhibit differing physical characteristics, particularly differing rotational stiffness.

There is a need to reduce the outer diameter of catheters by reducing their wall thickness, particularly those which are used in angiographic procedures, as well as other intravenous catheters. Catheters with reduced wall thickness penetrate smaller blood vessels with less trauma to blood vessel walls. The braided metal wire support which is typically carried in many such catheters clearly imposes a significant limitation on efforts to reduce the wall thickness. Accordingly, there is a significant need for a way to eliminate the metal support means in a catheter, while at the same time maintaining the necessary rotational and axial stiffness which is a major reason for the presence of such metal support means. If this can be accomplished, then the catheter outer diameter can be reduced to a dimension which is not possible when a metal support means is present, without reducing the lumen diameter, so that such catheters can penetrate more easily and more deeply into small arteries and the like without trauma to the artery wall.

By this invention, catheters and other tubing may be provided which do exhibit improved rotational stiffness by themselves, without the support provided by a braided wire sleeve or the like. Additionally, such catheters may be inherently stiffer in the longitudinal (axial) direction as well if desired, but to a degree which is relatively unrelated to the rotational stiffness, and which may be varied with respect to the rotational stiffness. Furthermore, improvements in strength of the catheter may also be provided. Also, the physical properties of the catheter of this invention may vary along the length thereof in a predetermined manner as may be deemed beneficial for the utility thereof.

DESCRIPTION OF THE INVENTION

By this invention, plastic tubing may be manufactured by extrusion of a plastic material through a tube extrusion die, the die having an outer wall or orifice to define the extruded tube outer diameter and an inner wall or mandrel to define the extruded tube inner diameter.

In accordance with this invention, one extrudes a tube of liquid crystal polymer plastic-containing material through the tube extrusion die, while rotating the orifice and mandrel relative to each other. As the result of this, the tube of liquid crystal polymer plastic-containing material exhibits at least a degree of circumferential orientation, in which the linear molecules of the liquid crystal polymer are to some extent circumferentially disposed by the orifice and mandrel rotation, while becoming substantially parallel to each other. This, in turn, causes the tube of liquid crystal polymer plastic-containing material to exhibit an increased amount of rotational stiffness in at least that section of the tubing in which the liquid crystal molecules are so oriented. Desired axial stiffness can also be achieved.

Further in accordance with this invention, one may coat the extruded liquid crystal polymer-containing material, preferably by coextrusion or subsequent extrusion, with a layer of a typically non-liquid crystal polymer formulation which preferably has tissue compatible characteristics, to provide such desirable characteristics to the catheter of this invention. Typically, the coating of polymer may be placed on the outside immediately after extrusion of the tube. Also or alternatively, the coating may be on the inner surface of the tube of liquid crystal polymer material.

If desired, the rotation rate of the outer and inner walls (orifice and mandrel) may be varied as the tube is extruded, with the result that various sections of the extruded tube, typically forming a catheter, exhibit differing, predetermined rotational stiffness. For example, it may be desired as the distal end of the catheter is extruded for the rotational rate of the outer and inner walls (orifice and mandrel) to be low or even zero, while the freshly extruded catheter tube is longitudinally oriented by stretching. This can cause the orientation of the liquid crystal polymer at the distal tube end to be substantially longitudinal, to provide a catheter section of relatively low rotational stiffness and relatively high longitudinal stiffness. Such a physical property is desired for a distal catheter tip, to facilitate advancement through small arteries or veins.

However, when the remainder of the catheter tube is being extruded, it may be desired to utilize a substantial rotation rate of the outer and inner walls of the extrusion die, to provide a substantial degree of circumferential orientation; ie: the liquid crystal molecules typically extend in a helical direction of orientation. This provides an increased amount of rotational stiffness along the main body of the extruded catheter. Because of this increased amount of rotational stiffness, it becomes possible to dispense with the braided wire sleeve which, in turn, permits the catheter wall to be thinner, for a reduction in outer diameter without a decrease in the diameter of the catheter lumen.

It can be seen that the desired characteristics of rotational stiffness and other properties may be varied in a manner which is dependent upon the rotation rate between the inner and outer walls (mandrel and orifice) of the extrusion die, and the speed with which the tube is stretched longitudinally, so that catheters of variable characteristics as desired may be manufactured in accordance with this invention.

A "liquid crystal polymer" is a type of polymer which is known to the art and is discussed in the literature. See for example the article by J. L. White and John F. Fellers, entitled Macromolecular Liquid Crystals and Their Applications to High Modulus and Tensile Strength Fibers, Journal of Applied Polymer Science: Applied Polymer Symposium 33, 137–173 (1978), or G. W. Farell and J. F. Fellers entitled A Rotating Annular Die To Control The Biaxial Orientation In Melt Processed Thermotropic Liquid Crystalline Cellulose Derivatives, Journal of Polymer Engineering, Vol 6, Nos. 1–4 (1986), pp. 263–289. See Also the article by D. G. Baird and R. Ramanathan entitled The In-Situ Generation Of Liquid Crystalline Reinforcements In Engineering Thermoplastics, From Multiphase Macromolecular Systems, B. M. Culbertson, editor, Japanese published Patent Application No. 63-199622 of Fujii et al. and see the article by M. Meier entitled The Extrusion Of Liquid Crystal Polymers, ANTEC, 1989 pp. 200-202.

Liquid crystal polymers are rigid, rod-like macromolecules, typically containing a substantial number of polyvalent aromatic groups such as phenylene. Liquid crystal polymers may be placed into a force field such as shear, in molten state or in solution, to be aligned and oriented, and they tend to retain their orientation on cooling or evaporation of solvent to effect hardening. This is because of the steric hinderance of molecular rotation provided by the large number of polyvalent aromatic or other groups. Thus they exhibit a high "relaxation time", which means that they tend to retain their orientation in the molten state after being placed therein by shear or elongational forces.

Generally, liquid crystal polymers are rather stiff in the solid state.

One preferred example of a liquid crystal polymer which may be made is a mixture of 20 to 40 percent of a poly(ethylene terephthalate) prepolymer which is reacted with 60 to 80 percent by weight of p-hydroxybenzoic acid. The resulting polymer may preferably have a molecular weight on the order of 40,000 to 200,000, and exhibits the desired characteristic of being capable of rather stable shear-orientation while in molten or other fluid condition, substantially retaining such orientation as the resulting material solidifies by either cooling or evaporation of fluidizing solvent. Thus, such materials may be extruded in accordance with this invention with rotational shear in combination with elongational force, to retain a helical orientation of the molecules for improved rotational and axial stiffness as desired. Another suitable liquid crystal polymer is a terepolymer of hydroxybenzoic acid, ethylene glycol, and terephthalic acid.

Other examples of liquid crystal polymers are VECTRA sold by Hoechst-Celanese, or HX materials sold by DuPont. Other liquid crystal materials include XYDAR sold by Amoco Company, and any other polymer material having a rod like molecule and thus exhibiting ". . . an inherent propensity to align more readily during melt flow than flexible chain polymers". (See the Baird et al. article cited above, page 2). Specifically, a Liquid Crystal Polymer has more of such "inherent propensity to align" than poly(ethylene terephthalate).

Other liquid crystal polymers which may be used include liquid crystal polymers containing divalent naphthalene moieties along the backbone. Hydroxypropyl cellulose is a liquid crystal type, water soluble polymeric material that may be used in accordance with this invention in certain circumstances. Other materials which are liquid crystal polymers include many aromatic polyurethanes, polyethersulphones, polyamides and polyesters, particularly the aromatic copolyesters. For example, a thermal liquid crystal polymer may be made from poly(ethylene terephthalate) and acetoxybenzoic acid. Many other liquid crystal materials are disclosed in Japanese published Patent Application No. 63-199622, being typically polyester type materials.

One liquid crystal polymer plastic-containing material which is used to form a catheter in accordance with this invention may be a blended mixture of liquid crystal polymer or polymers (typically about 10 to 40 percent by weight), with the balance of the blended material including typically softer materials, for example polyurethanes such as PELLETHANE ®, polyamides such as nylon 6, 6/6, 6/10, 11, 12, 12/10, 12/12 and other polyamides, polyesters such as PET, and polyester elastomers such as HYTREL ® polyester, or polyamide elastomers such as PEBAX ®. Additionally, other blending materials may include polystyrene or other styrene copolymers, polyethylene, polypropylene, or copolymers of ethylene with other vinylic polymers such as propylene, acrylates, or the like.

The extruded tube of liquid crystal polymer plastic-containing material may be coated, typically an exterior coating but alternatively or additionally a coating of the inner lumen as well. The coating may be a smooth, hemocompatible surface plastic material which may have lubricating characteristics, and may contain antiinfective additives or any other desired medication or the like as described in Rowe U.S. patent application Ser. No. 322,929, filed Apr. 3, 1989. such coating materials may include softer polyurethanes, hydrophilic polyurethanes, urethane-silicone blends, urethane-fluoropolymer copolymers, vinyl polymers, acrylates such as polyHEMA, or other bio/hemocompatible polymers. The coatings may contain biological materials such as heparin or drugs as needed to achieve the desired hemocompatability or other desirable characteristics of the catheter coating.

The tubular catheter body may then have applied to it the customary parts, connections and the like used in the manufacture of conventional catheters of every type.

If desired, tubes extruded in accordance with this invention for catheters or any other use may be biaxially oriented in that they may be longitudinally stretched, simultaneously with rotation of the extrusion die to provide circumferential orientation. The direction of orientation is helical in such circumstance about the extruded tubing.

In many circumstances, catheters or other tubes made of substantially pure liquid crystal polymer are likely to be unduly stiff or be otherwise less than optimum in their physical properties. Accordingly, it is generally preferred for the liquid crystal polymer plastic-containing material to comprise from to 40 weight percent of a liquid crystal plastic, and from 60 to 99 weight percent of a different structural plastic matrix, with the materials being dispersed together to form the liquid crystal polymer plastic-containing material. Preferably, the liquid crystal polymer defines, at the temperature of its extrusion and also its temperature of use, a separate phase from the structural plastic matrix with the liquid crystal polymer being dispersed in the structural plastic matrix in small volume domains or droplets. Thus, preferably, on extrusion with rotational shear and elongational force as described above, the separate phase of liquid crystal plastic forms generally helically extending, separate fibrils within the extruded tube, with the fibrils being dispersed in the structural plastic matrix. Hence, the catheter of this invention may include its own, in situ reinforcing members, analogous to a structural wire reinforcement but made from an integral part of the liquid crystal polymer plastic-containing material.

The fibrils thus formed preferably exhibit an aspect ratio of about 10 to 300, the aspect ratio being defined by the length of the fibril divided by its diameter. Preferably, the aspect ratio may be on the order of 50 to 200. Also, it is generally preferred for the liquid crystal polymer plastic-containing material to contain from 5 to 35 weight percent of the liquid crystal polymer, with most or all of the balance being the structural plastic matrix. Other ingredients or additives may be provided to accomplish any desired purpose such as internal lubricants, pigments, radiopaque agents, surfactants, and the like.

Specific examples of the structural plastic matrix which may be used may include polyurethanes, polyamides, polyesters, polysulphones, polyethylene, polypropylene, thermoplastic elastomers such as Kraton brand elastomer, and the like.

The liquid crystal polymer ingredient may be desirably incompatible or semi-compatible with the particular structural plastic matrix which was chosen for use, so that a mixture of, for example, 15 percent by weight of liquid crystal polymer with up to 85 percent by weight of structural plastic matrix, when heated may form a mixture which is sufficiently apparently homogeneous that, while the mixture comprises two phases, the distribution of liquid crystal polymer is in the form of droplets in the structural plastic matrix, rather like an emulsion. When such a mixture is extruded through the tube extrusion die in which the outer and inner walls (orifice and mandrel) rotate with respect to each other, the liquid crystal droplets are stretched and elongated by the circumferential and elongational stresses to typically form the generally helically extending fibrils within an extruded tube manufactured in accordance with this invention.

Thus, the liquid crystal fibrils extend and are oriented in such a helical direction to provide new properties to the resulting extruded tube from what would otherwise be provided by a tube of pure, structural plastic. Particularly, the liquid crystal plastic below its softening point is typically relatively hard, and thus behaves in a manner similar to an array of reinforcing metal fibers in the extruded tube, to increase the torsional stiffness and the overall strength of the structure.

As a further advantage, the above advantages are achieved while at the same time radio frequency generated heating may be used for shaping and welding of a catheter utilizing such tubing because the helical fibrils present are non-metallic. Additionally, a significantly simplified manufacturing process is provided, since the manufacturing step of installing a metal wire sleeve is typically not used. Thus, the wall thickness may be reduced, as previously stated.

Accordingly, a catheter having good physical properties is provided, but the outer diameter can be reduced by a reduction in wall thickness, to generate less trauma on insertion, and to allow for navigation of even smaller and more tortuous paths. If desired, as previously described, an added layer of a polymer formulation having tissue compatible (including blood compatible) characteristics may be placed either over or within (or both) the liquid crystal polymer plastic-containing tube of this invention.

The term "tissue compatible characteristics" includes characteristics provided by appropriate plastic which cause them to be well tolerated by living cells. Such plastics may which carry desired medications, antithrombogenic agents, or possess any other medical benefit which makes it desirable to place it as a layer as a coating over or within the liquid crystal polymer-containing tube. Such an added layer can be extruded onto the liquid crystal polymer-containing tube as an added extrusion step, if desired, immediately following the original extrusion of the liquid crystal polymer containing tube. Such overcoating extrusion processes are conventional per se.

DESCRIPTION OF THE DRAWINGS

In the drawings, FIG. 1 is a schematic view of a process for manufacturing catheter tubing in accordance with this invention;

FIG. 2 is a fragmentary detailed sectional view of an extruder as shown in FIG. 1; and FIG. 3 is a perspective view of a portion of the catheter tubing produced by the process of this invention.

DESCRIPTION OF SPECIFIC EMBODIMENT

Referring to the drawings, FIGS. 1 and 2 show an overall process for manufacturing a catheter. A liquid crystal polymer plastic-containing material may be made from 70 to 90 parts by weight of a soft, flexible polyurethane formulation, intimately mixed with 10 to 30 parts by weight of a liquid crystal polymer made by the polymerization reaction between 30 weight percent of poly(ethylene terephthalate) prepolymer reacted with 70 weight percent of p-hydroxybenzoic acid, resulting in a liquid crystal polymer having a molecular weight on the order of 100,000.

Alternatively, the liquid crystal polymer may be VECTRA B950, sold by Hoechst-Celanese Co., this liquid crystal plastic being present in 10, 20, or 30 percent concentration by weight, with essentially all of the balance of the liquid crystal polymer plastic-containing material being essentially all a structural plastic matrix material such as nylon 12, LOMAD PET type polyester elastomer, sold by General Electric, or an elastomeric polyurethane.

This softened plastic mixture is extruded through first extruder 10, with the soften®d plastic entering the extruder through inlet 12 to be formed into a tube by passing through cylindrical chamber 14. Then, cylindrical mass of heated plastic material is extruded through the circular opening 16 which is defined between extruder orifice 18 and mandrel 20, to form plastic tubing 22.

As the extruder operates, orifice section 18 is rotated at a predetermined rate by chain drive 24 which is linked to a conventional power source 26, shown in schematic manner. At the same time, plastic tubing 22 is longitudinally stretched by conventional tube stretching apparatus 28 (also shown schematically) so that the plastic exiting from annular opening 16 is not only rotationally oriented by the rotating of orifice section 18, but it also may be longitudinally oriented by the stretching provided by apparatus 28.

Alternatively or additionally, mandrel 20, which defines the inner wall of the cylindrical extrusion orifice 16, may be rotated, and typically counter-rotated in the rotational direction opposite to the direction of rotation of orifice 18, being driven by chain drive 32 and schematically illustrated power source 34. Thus, a strong amount of rotational orientation can be provided to both the inner and the outer surfaces of extruded tubing 22, to accomplish the purposes of this invention.

Extruded tubing 22 then may pass to a second, coating extruder 36, of conventional design, to typically provide tubing 22 with an outer layer of a flexible plastic having good antithrombogenic characteristics, for example poly(ethylene terephthalate), or any other desired material, optionally containing an added medical agent such as heparin. The coated tubing 22a, having an outer coating 38 of tissue compatible material as described above, may then be sent to a further manufacturing station, symbolically indicated by reference numeral 40, where the tubing may be cut to length and fabricated into catheters by conventional means.

Outer layer 38 may be simply a thin coating, for example a coating having a thickness of 0.01 inch, or any other thickness as may be appropriate for the particular circumstance.

The specific liquid crystal polymer plastic-containing material which is extruded in accordance with this invention preferably exhibits dispersed droplets of liquid crystal polymer in the structural plastic matrix, as an incompatible, two phase material. Accordingly, when tubing 22 is extruded with rotational shear b rotation of either or both of orifice 18 and mandrel 20, the individual droplets of liquid crystal polymer tend to elongate into linear, helically extending fibrils 42, 44 dispersed in the structural plastic, for example fibrils having an aspect ratio on the order of 30. It can be seen from FIG. 3 that the fibrils of portion 46 of tube 22 follow a helical path which defines a greater angle to the longitudinal axis of tubing 22a than do the fibrils 44 in section 48 of tubing 22a. This may be accomplished by varying the speed of relative rotation between orifice 18 and mandrel 20 as the tubing 22 is extruded. A greater speed of rotation will result in a higher angled helical arrangement of fibrils 42, while a lower relative speed of rotation will result in the lower angle of fibrils 44 to the longitudinal axis of tubing 22a. Accordingly, the physical characteristics of tubing section 46 can vary substantially from the physical characteristics of tubing section 48, although they constitute sections of the same piece of tubing. Specifically, the longitudinal stiffness and the rotational stiffness of the tubing sections can be varied by variation of the helical angle of the fibrils to the longitudinal axis of tubing 22a, so that desired portions of the tubing may have certain properties, and other portions of the catheter may have different physical properties, particularly differing longitudinal stiffness and rotational stiffness, since both of these properties are influenced by the angle of the fibrils 42 or 44 to the tubing axis. Typically, the fibril helical angle may vary between 10 and 60 degrees.

If desired, tube 22 may be extruded with no relative rotation between orifice 18 and mandrel 30, but with stretching imposed by orienting apparatus 28, With the result that the fibrils of such tubing are generally parallel to the tubing axis. Such a structure tends to have relatively high longitudinal stiffness, but such fibrils make little contribution to the rotational stiffness, so that such a structure will have a rotational stiffness that approximates that of the particular structural plastic matrix used. With high rotation, the helically disposed fibrils 42 exhibit a relatively high angle to the tubing axis, to provide tubing which ha increased rotational stiffness.

Making use of the invention of this application, it becomes possible to provide a "steerable" catheter having substantial rotational stiffness along most of its length by the presence of helical fibrils 42 at a substantial angle to the tubing axis, so that the conventional braided metal sleeve found in steerable catheters is not required. At the same time, the distal tip of the catheter ma exhibit fibrils of relatively low angle to the tubing axis, so that the tip exhibits increased longitudinal stiffness while being of less rotational stiffness, to provide an intravascular catheter having desirable, tailor made properties for use out of one piece of extruded tubing.

The above has been offered for illustrative purposes only, and is not intended to limit the scope of the invention of this application, which is as defined in the claims below.

What is claimed is:

1. In an extruded plastic catheter which defines a tubular catheter body, the improvement comprising, in combination:

said catheter body being substantially defined by an extruded, tubular first layer, said first layer comprising, intermixed together, from 1 to 40 weight percent of a liquid crystal polymer and 60 to 99 weight percent of a different, softer structural plastic matrix which is not a liquid crystal polymer, said liquid crystal polymer defining a separate phase from said structural plastic matrix, said first layer exhibiting at least a degree of circumferential orientation to provide an increased amount of rotational stiffness to at least a section of said catheter body, said separate phase of the liquid crystal polymer defining generally helically extending fibrils dispersed throughout essentially the entire volume of said first layer, said fibrils being formed from liquid crystal polymer plastic droplets dispersed in said structural plastic matrix.

2. The catheter of claim 1 in which said catheter body carries a second layer of a polymer formulation having tissue compatible characteristics.

3. The catheter of claim 1 in which various sections of said catheter body exhibit differing degrees of circumferential orientation of said fibrils and rotational stiffness.

4. The catheter of claim 1 in which said fibrils generally exhibit an aspect ratio of 10 to 300.

5. The catheter of claim 1 in which said liquid crystal polymer exhibits a greater propensity than poly(ethylene terephthalate) to orient during melt flow and to retain such orientation.

6. The catheter of claim 1 in which said catheter body is free of any added fibrous support means.

7. The catheter of claim 1 in which said liquid crystal polymer comprises a prepolymer of poly(ethylene terephthalate), reacted with p-hydroxybenzoic acid.

8. The catheter of claim 1, in which said liquid crystal polymer plastic-containing material comprises from 5 to 35 weight percent of said liquid crystal polymer.

9. The catheter of claim 1 in which said liquid crystal polymer is a terpolymer of hydroxybenzoic acid, ethylene glycol, and terephthalic acid.

10. The catheter of claim 1 in which substantially all of said fibrils extend longitudinally along said tube for no more than a minor portion of the length thereof.

11. An extruded plastic tubing which defines a tubular body, said tubular body defining a tubular layer which comprises a mixture of a minor portion of a liquid crystal polymer and a major portion of a structural plastic matrix which is not a liquid crystal polymer, said liquid crystal polymer defining a separate phase from said structural plastic matrix with the structural plastic matrix and the liquid crystal polymer phases comprising a blended mixture which is dispersed together, said tubular layer exhibiting at least a degree of circumferential orientation to provide an increased amount of rotational stiffness to at least a section of said tube, the separate phase of said liquid crystal polymer defining generally helically extending fibrils dispersed throughout essentially the entire volume of said tubular layer.

12. The plastic tube of claim 11 in which said structural plastic matrix is made of a softer material than said liquid crystal polymer.

13. The plastic tube of claim 11 which comprises from 1 to 40 weight percent of said liquid crystal polymer and 60 to 99 weight percent of said structural plastic matrix.

14. The plastic tube of claim 11 in which said fibrils generally exhibit an aspect ratio of 10 to 300.

15. The plastic tube of claim 11 in which said liquid crystal polymer exhibits a greater propensity than poly(ethylene terephthalate) to orient during melt flow and to retain such orientation.

16. The plastic tube of claim 11 in which said catheter body is free of any added fibrous support means.

17. The plastic tube of claim 11 in which said liquid crystal polymer comprises a prepolymer of poly(ethylene terephthalate), reacted with p-hydroxybenzoic acid.

18. The plastic tube of claim 11 in which said liquid crystal polymer plastic-containing material comprises from 5 to 35 weight percent of said liquid crystal polymer.

19. The plastic tube of claim 11 in which substantially all of said fibrils extend longitudinally along said tube for no more than a minor portion of the length thereof.

* * * * *